United States Patent
Dopatka

(10) Patent No.: US 6,664,070 B1
(45) Date of Patent: Dec. 16, 2003

(54) WASHING SOLUTION FOR SOLID-PHASE IMMUNOMETRIC METHODS WHICH CONTAINS STABILIZERS FOR THE LABELING SYSTEM, AND THE USE THEREOF

(75) Inventor: Hans-Detlef Dopatka, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/195,048

(22) Filed: Feb. 14, 1994

Related U.S. Application Data

(63) Continuation of application No. 07/798,193, filed on Nov. 26, 1991, now abandoned.

(30) Foreign Application Priority Data

Nov. 28, 1990 (DE) .......................... 40 37 764

(51) Int. Cl.[7] .............................. G01N 33/53
(52) U.S. Cl. .................. 435/7.92; 435/14; 435/21; 435/25; 435/26; 435/28; 435/962; 435/967
(58) Field of Search .................. 435/7.92, 14, 21, 435/25, 26, 28, 962, 967

(56) References Cited

U.S. PATENT DOCUMENTS

| | | | | |
|---|---|---|---|---|
| 4,132,598 A | * | 1/1979 | Modrovich .................. | 435/21 |
| 4,487,830 A | * | 12/1984 | Coates et al. ................ | 435/7.9 |
| 4,496,654 A | * | 1/1985 | Katz et al. .................... | 435/7.5 |
| 4,521,511 A | * | 6/1985 | Stout .......................... | 435/28 |
| 4,598,044 A | * | 7/1986 | Kricka et al. ................ | 435/7.9 |
| 4,810,630 A | * | 3/1989 | Craig et al. ............. | 436/825 X |
| 4,828,983 A | * | 5/1989 | McClune .................. | 435/28 X |
| 5,176,999 A | * | 1/1993 | McClune et al. ............ | 435/7.5 |

FOREIGN PATENT DOCUMENTS

| | | |
|---|---|---|
| DE | 3541978 | 11/1985 |
| DE | 3541979 | 11/1985 |
| DE | 3638767 | 11/1986 |
| EP | 0 431 682 A2 | 6/1991 |

OTHER PUBLICATIONS

Voller, A et al. Enzyme–Linked ImmunoSorbent Assay. In: Manual of Chlinical Laboratory Immunology, 3rd Edition. (Rose et al., Eds), Washington, DC: American Society For Microbiology, 1986. Pp. 99–109.*
European Search Report dated Mar. 27, 1992.
Japanese Patent Publication No. 2–161357—Jun. 21, 1990.
Patent Abstracts of Japan, vol. 14, No. 415 (P–1102) (4358) Sep. 7, 1990 (Abstract of Japanese Publication No. 2–161357 above).
Kyrein, H.J. (1978) Arztl. Lab. 24, pp. 67–65.
Voller, A. et al. (1976) Bull. World Health Organ., 53, pp. 55–65.
Burrows, P.M. et al. (1984). Virol. Meth. 8, pp. 207–216.
Krishna et al. (1980) J. Clin. Microbiol. 12, pp. 46–51.
Chou et a. J. Clin. Microbiol. 25, pp. 52–55.
Ziegelmaier et al. (1981) J. Biol. Standard. 9, pp. 23–33.

* cited by examiner

*Primary Examiner*—Lynette R. F. Smith
*Assistant Examiner*—Ginny Allen Portner
(74) *Attorney, Agent, or Firm*—Finnegan, Henderson, Farabow, Garrett and Dunner, L.L.P.

(57) ABSTRACT

A washing solution for solid-phase immunometric methods which contains stabilizers for the labeling system, and the use thereof

6 Claims, 2 Drawing Sheets

CORRELATION OF REPRODUCEBILITY
WASHING-SOLUTION WITHOUT PHENOL

Fig. 1: SEQUENCE AND RESULTS OF ELISA USING INSTRUMENTATION FOR THE WASHING-STEP
CORRELATION OF SIGNAL
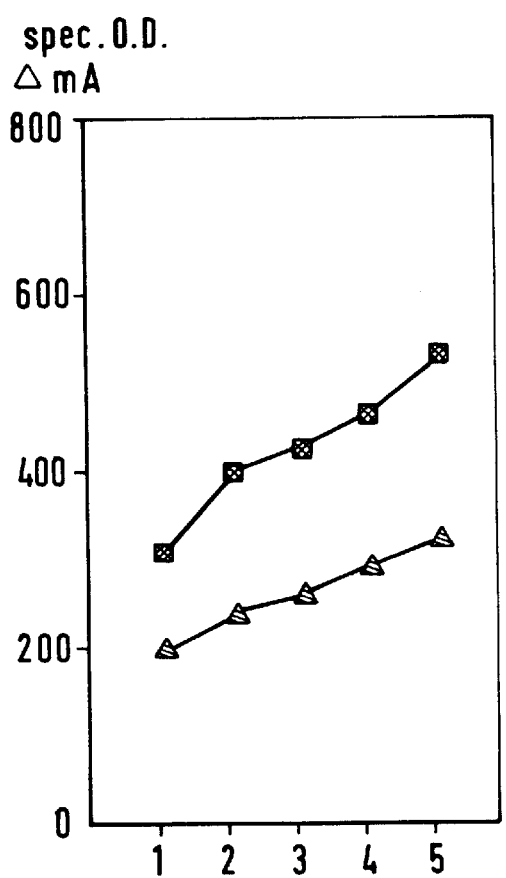
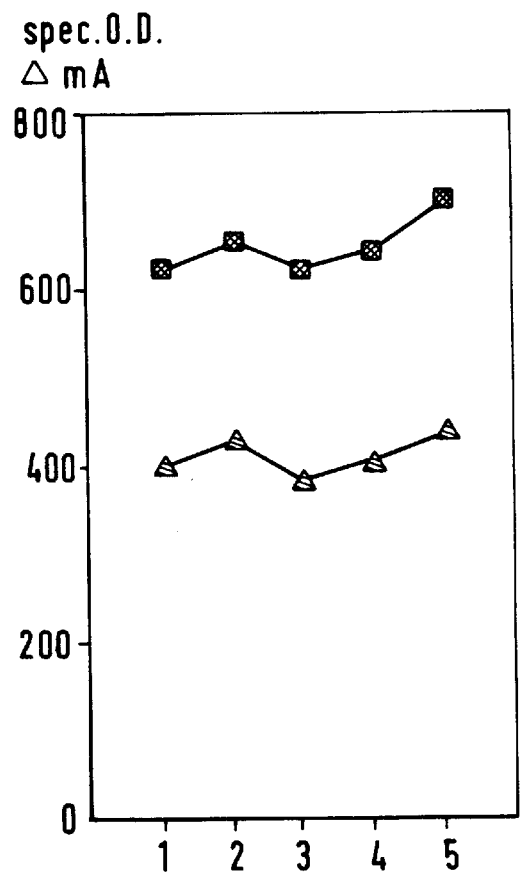
SEQUENCE OF THE MICROTITRATIONPLATES
—■— PP 1635-3    —△— S 81-184 c1
WASHING - SOLUTION
WITHOUT PHENOL    WITH PHENOL
Fig. 1A    Fig. 1B

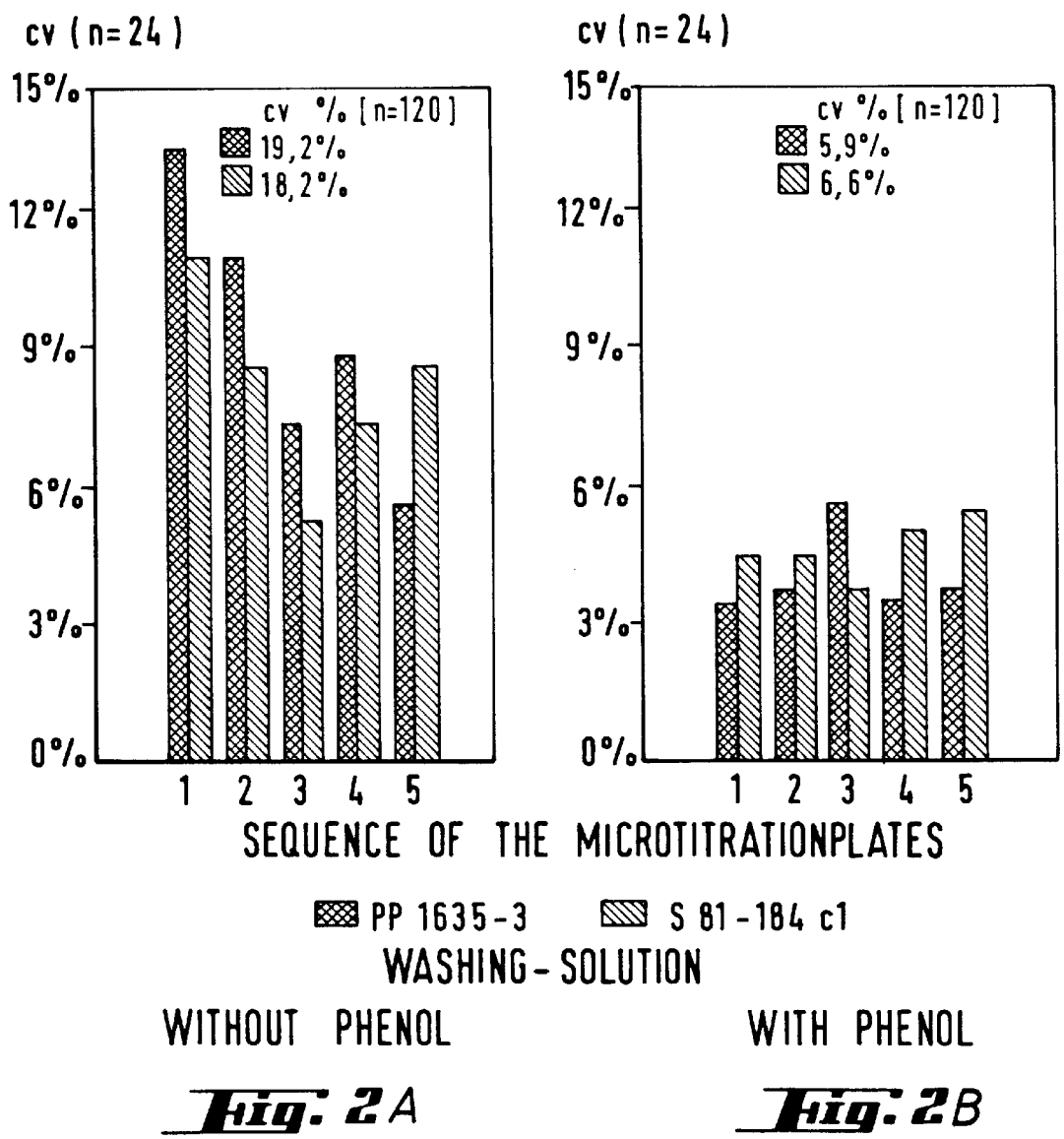
Fig. 2: SEQUENCE AND RESULTS OF ELISA USING INSTRUMENTATION FOR THE WASHING-STEP

WASHING SOLUTION FOR SOLID-PHASE IMMUNOMETRIC METHODS WHICH CONTAINS STABILIZERS FOR THE LABELING SYSTEM, AND THE USE THEREOF

This application is a continuation of application Ser. No. 07/798,193 filed Nov. 26, 1991, now abandoned.

The invention relates to a washing solution, containing stabilizers for the labeling enzyme, for solid-phase immunometric assays, and to the use of this washing solution. Specifically the stabilizers for enzymes are phenol and phenol derivatives.

Solid-phase immunometric assays, for example the enzyme-linked immunosorbent assay (ELISA), require one or more washing steps in the procedure. This entails the solid phase being rinsed with the washing solution in order to remove substances which have undergone nonspecific attachment, for example immunoglobulins, or excess reagents, for example an enzyme conjugate. If this is carried out in a suitable manner, the result of the assay is a measured signal which corresponds to the concentration of the detected analyte. In addition, this result can be reproduced.

Enzyme immunoassays as such are known to the person skilled in the art and described in the literature, see, for example, KYREIN, H. J., Ärztl. Lab. 24, 57–65 (1978).

Solid phases for use in such enzyme immunoassays are likewise known to the person skilled in the art and described in the literature, see, for example, VOLLER, A. et al., Bull. World Health Organ. 53, 55–65 (1976).

Such solid-phase immunometric assays can also be completed using instruments. This entails the washing steps being carried out by the instrument. The known washing solutions, which are composed, for example, of detergent-containing phosphate buffers in the neutral range, have certain disadvantages in these systems. When such instruments, are used to complete the washing step, both the accuracy and the reproducibility of the measured signal reach an acceptable level only after some time, i.e. after some plates have been completed (BURROWS, P. M. et al., J. Virol. Meth. 8, 207–216 (1984)).

The present invention was therefore based on the object of finding a washing solution whose use., in instruments makes possible correct completion of the ELISA even on immediate use of these devices. A measured signal which correlates with the concentration of the detected analyte, and the reproducibility of the results obtained, are regarded as criteria for correct assay procedure.

Instruments within the meaning of this invention are all instruments with whose aid washing steps in enzyme immunoassays can be carried out mechanically, irrespective of whether these instruments are able to carry out further steps in completing ELISA assays.

It has now been found, surprisingly, that the addition of stabilizers achieves this object, irrespective of the buffer basis, the pH or other additives to the washing solution.

Stabilizers within the meaning of this invention are substances which stabilize the labeling enzyme, such as, for example, tobramycin, phenol and phenol derivatives, and phenols and phenol derivatives which carry one or more substituents, which can be $C_1$–$C_3$-alkyl, chlorine and/or bromine, are preferred.

It is also generally possible to stabilize enzymes by substrates and competitive inhibitors.

The invention therefore relates to a washing solution for heterogeneous enzyme immunoassays which contains a stabilizer for the marker enzyme.

The invention also relates to the use of a washing solution as described above in a heterogeneous enzyme immunoassay.

The invention further relates to heterogeneous enzyme immunoassays entailing the use of a washing solution as described above in at least one washing step.

The invention furthermore relates to the use of stabilizers for the labeling enzyme in washing solutions for heterogeneous enzyme immunoassays.

The stabilizer is added in a concentration of 0.01 to 20 mM. A concentration of 0.1 to 5 mM is preferred, and 1 mM is very particularly preferred. The stabilizer can be added to previously known washing solutions or buffers for solid-phase immunometric assays.

In a preferred embodiment, the washing solution is buffered. Buffer systems which can be used for this are known to the person skilled in the art. The specific pH used depends on the assay system and can be determined where appropriate by experiment.

Preferred stabilizers are phenols and phenol derivatives, in which case phenol can also carry one or more substituents which can be $C_1$–$C_3$-alkyl groups and chlorine and/or bromine atoms.

The solutions described in the examples are particularly preferred, and phenol is very particularly preferred.

Heterogeneous enzyme immunoassays are known per se to the person skilled in the art. They can be used to detect antigens and antibodies and can be additive, such as, for example, a sandwich immunoassay, or competitive. The various possible embodiments have been adequately described in the literature. The ELISA method is preferred within the scope of the invention.

Marker enzymes for enzyme immunoassays as such are disclosed in the literature, and alkaline phosphatase, β-galactosidase and horseradish peroxidase are preferably used, and horseradish peroxidase is particularly preferably used.

Solid phases for heterogeneous enzyme immunoassays are known per se to the person skilled in the art, and concave shaped articles such as, for example, tubes or wells, convex shaped articles such as, for example, beads, stars or the like and microparticles (particle size<1,000 nm) such as, for example, latex particles and magnetically attractable particles are preferably used. Particularly preferred in this context are wells in the form of microtiter plates, latex particles and magnetically attractable particles. Microtiter plates are very particularly preferred.

Materials for solid phases are known to the person skilled in the art. Unless already fixed by the nature of the solid phase, such as, for example, in the case of latex particles, polystyrene is preferably used.

Buffer systems for use in enzyme immunoassays are known to the person skilled in the art. The person skilled in the art is also aware that the nature of the buffer system used in each case depends inter alia on the pH to be achieved.

Detergents for use in washing solutions for heterogeneous enzyme immunoassays are likewise known to the person skilled in the art (see, for example, VOLLER, A. et al., Bull. World Health Organ. 53, 55–65 (1976)), and non-ionic and zwitterionic detergents are preferably used; polyoxyethylenes are particularly preferred, and $^R$Tween 20 is very particularly preferred.

Neutral proteins for use in enzyme immunoassays are known to the person skilled in the art; examples which are preferably used are serum albumins, gelatin, chemically modified gelatin such as, for example, polygeline, and milk proteins such as, for example, lactoferrin, particularly preferred are human or bovine serum albumin, polygeline and lactoferrin, very particularly preferred are polygeline and lactoferrin, the latter prepared as described in German Patent Application 36 38 767.

The person skilled in the art is aware that neutral salts such as, for example, NaCl are added to solutions used in enzyme immunoassays in order to adjust to a defined osmolarity.

Said substances are employed in aqueous solution for use; until used they can be, for example, in lyophilized or granulated form, as dry mixture or in liquid form as final dilution or concentrate.

A preferred embodiment of the washing solution according to the invention has the following composition:

| Buffer | 0 ... 100 mmol/l, preferably 10–20 mmol/l, very preferably 10 mmol/l |
|---|---|
| Detergent | 0 ... 1%, preferably 0 ... 0.2%, very preferably 0.1% (w/v) |
| Neutral protein | 0 ... 1% (w/v) |
| Stabilizer | 0.1 ... 20 mmol/l, preferably 1 mmol/l. |

The composition and components of conventional washing solutions are known to the person skilled in the art.

One example of them is a 10 mM phosphate buffer composed of $Na_2HPO_4$, $KH_2PO_4$, NaCl 0.45% w/v and 0.1% (w/v) Tween$^R$ 20 with a pH of 6.5. This washing solution was mixed according to the invention as example with 1 mM phenol and was used to demonstrate the improvement in the measured signal and in the reproducibility achieved therewith in the ELISA.

The following example serves only for illustration and in no way represents a restriction.

EXAMPLE

An ELISA for detecting IgM against human cytomegalovirus (CMV) was chosen as solid-phase immunometric assay. Polystyrene microtiter plates with 96 reaction wells in an 8×12 field were used as solid phase.

CMV cultured in human embryonic fibroblasts, and human embryonic fibroblasts not infected with CMV, were processed by the method of Krishna et al. (1980), J. Clin. Microbiol. 12, 46–51, to preparations which are called hereinafter CMV antigen and (negative) control antigen respectively.

Each microtiter plate was then coated by pipetting 0.1 ml of CMV antigen solution into a reaction well, and 0.1 ml of control antigen solution into an adjacent reaction well, according to the method of the abovementioned authors, in such a way that rows of reaction wells alternately coated for CMV antigen and control antigen were produced. Several assay plates were prepared in the same production cycle in this way.

The prior dilution and the pipetting in of 0.15 ml of the test samples in each case always took place in parallel in adjacent reaction wells which were coated in one case with the CMV antigen and in the other case with the control antigen in accordance with the instructions of Chou et al. (1987), J. Clin. Microbiol. 25, 52–55.

The completion of the ELISA very substantially followed the procedure described by Ziegelmaier et al. (1981), J. Biol. Standard. 9, 23–33, of sample incubation, conjugate incubation and substrate incubation, all these reaction phases (2) and (3) being preceded by a washing step.

Assay Protocol:
Coating of the solid phase with viral antigen

Washing step*)
Step 1: 150 μl**) of test serum in dilution buffer for serum and conjugate (DBSC) are incubated at 37° C. (for IgG and IgM)
Washing step
Step 2: 50 μl of anti-human IgG × AP conjugate in DBSC, 60 min at 37° C.
Washing step
Step 3: 100 μl of p-nitrophenyl phosphate (p-NPP) in substrate buffer, 45 min at 20–25° C.
Step 4: 50 μl of 2N NaOH Optical evaluation
*)in each case 3 × 200 μl of washing buffer within 5 min
**)volumes stated in each case per well These washing steps can be carried out not only manually with a washing comb but also automatically with a device which is connected to a washing solution storage vessel. Examples complying with the state of the art in this connection are the Ultrawasher II from DYNATECH, the Microplate Washer from Flow Laboratories, the Immuno Washer NK 350 from NUNC, the Easy Washer "EAW plus" from SLT LABINSTRUMENTS or the Behring ELISA processor of Behringwerke. The device mentioned last was used in the example which is presented.

As a modification of the procedure of Ziegelmaier et al., an anti-human IgM conjugate with peroxidase as marker enzyme was used, not an anti-human IgG conjugate with alkaline phosphatase. The substrate chosen for this enzyme was tetramethylbenzidine plus hydrogen peroxide, which had been prepared as described in German Patent Applications 35 41 978 and 35 41 979. The development of color has been stopped after 30 min with 0.1 ml of 0.5 N sulfuric acid and measured at 450 nm in a suitable photo-meter, for example the Titertek$^R$, Multiskan MC, apparatus from Flow Laboratories or the Behring ELISA processor of Behringwerke. The apparatus mentioned last was used in the example which is presented.

The measured signal obtained with the test sample in the reaction well coated with control antigen was subtracted from the measured signal obtained from the same sample in the reaction well coated with CMV antigen. The difference (Δ E) is called the specific signal (spec. O.D.) and exclusively evaluated.

A simple experimental arrangement was chosen to illustrate the effect of the automatic addition of washing solution on the ELISA result, namely specific signal and its reproducibility.

An assay plate was coated in multiple replicates (n=24) only with two test samples. One sample was identified as PP 1635-3, and the other as S 81-184cl. Four other assay plates were made up with identical sample charging, and the ELISA was carried out with all five assay plates together.

Care was taken during this that the sequence of the individual assay plates, one to five, remained unchanged in the resulting washing steps.

BRIEF DESCRIPTION OF THE DRAWINGS

In the first place, starting from the arithmetic mean of the specific O.D., the signal height on each assay plate was depicted as a function of the washing sequence (FIG. 1A). It was unambiguously evident that the specific O.D. increases with the washing sequence of the assay plates.

Then, starting from the coefficient of variation (CV) of the specific O.D., the signal variation on each assay plate was depicted as a function of the washing sequence (FIG. 2A). It was unambiguously evident that the CV becomes lower, i.e. better, with the washing sequence of the assay plates.

If an identical experimental approach is carried out in such a way that phenol, for example 0.1 mM, is added according to the invention to the washing solution, and this washing solution is introduced by a device into the assay, the result is found to be surprisingly favorable.

The means of the specific O.D. are now, irrespective of the washing sequence of the assay plates, at the signal level corresponding to the concentration of the CMV-specific IgM (FIG. 1B). In addition, the signal variation is, irrespective of the washing sequence of the (FIG. 2B).

If the measurement variation obtained on all five assay plates (overall CV) is evaluated, the improvement, achieved according to the invention, in the reproducibility of the ELISA result is even more drastic. With a, washing solution according to the state of the art, the overall CV is 18 to 20% depending on the test sample employed. With a washing solution with the phenol addition according to the invention and the use thereof, the overall CV is 5 to 7% depending on the test sample employed.

What is claimed is:

1. A method for determining the amount of an analyte in a sample of a biological fluid, wherein said method is carried out by an instrument and comprises the following steps
   a) fixing a first antibody specific for said analyte to a solid phase;
   b) bringing said sample into contact with said immobilized first antibody;
   c) incubating analyte bound to said first antibody immobilized on said solid phase with a second antibody specific for said analyte, which second antibody carries an enzyme as label, wherein said enzyme is selected from the group consisting of peroxidase, alkaline phosphatase and β-galactosidase;
   d) washing said solid-phase with a washing solution where said washing solution contains phenol or a phenol derivative carrying one or more substituents, wherein said substituents are $C_1$ to $C_3$-alkyl groups, chlorine or bromine atoms;
   e) removing said washing solution; and
   f) determining the amount of label bound to said solid-phase.

2. The method of claim 1 wherein the Phenol or Phenol derivative is present in step d) in a concentration in the range of 0.01 to 20 mmol/l.

3. The method of claim 1, wherein said enzyme is peroxidase.

4. The method of claim 1, wherein an additional washing step is performed between step b) and step c).

5. The method of claim 1, wherein said enzyme is alkaline phosphatase.

6. The method of claim 1, wherein said enzyme is β-galactosidase.

* * * * *